(12) United States Patent
Park et al.

(10) Patent No.: US 9,829,441 B2
(45) Date of Patent: Nov. 28, 2017

(54) WAFER IMAGE INSPECTION APPARATUS

(71) Applicants: NEXTIN, INC., Seongnam-si (KR); SAMSUNG ELECTRONICS CO., LTD., Suwon-si (KR)

(72) Inventors: Tae Hoon Park, Yongin-si (KR); Segal Ram, Nes Ziona (IL)

(73) Assignees: NEXTIN, INC., Gyeonggi-Do (KR); SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/023,112

(22) PCT Filed: Nov. 27, 2014

(86) PCT No.: PCT/KR2014/011459
§ 371 (c)(1),
(2) Date: Mar. 18, 2016

(87) PCT Pub. No.: WO2015/080480
PCT Pub. Date: Jun. 4, 2015

(65) Prior Publication Data
US 2017/0003230 A1 Jan. 5, 2017

(30) Foreign Application Priority Data

Nov. 29, 2013 (KR) .................. 10-2013-0146941
Feb. 24, 2014 (KR) .................. 10-2014-0021568

(51) Int. Cl.
*G01N 21/00* (2006.01)
*G01N 21/88* (2006.01)
(Continued)

(52) U.S. Cl.
CPC ..... *G01N 21/8851* (2013.01); *G01N 21/8806* (2013.01); *G01N 21/9501* (2013.01);
(Continued)

(58) Field of Classification Search
CPC ......... G01N 21/9501; G01N 21/95607; G01N 21/956; G01N 2021/9513; G01N 21/21;
(Continued)

(56) References Cited

U.S. PATENT DOCUMENTS

| 7,027,142 B2 * | 4/2006 | Some | G01N 21/171 |
| | | | 356/237.1 |
| 7,180,586 B2 * | 2/2007 | Neumann | G01N 21/8806 |
| | | | 356/237.5 |

(Continued)

FOREIGN PATENT DOCUMENTS

| JP | H11194272 | 7/1999 |
| JP | 2000152281 | 5/2000 |

(Continued)

OTHER PUBLICATIONS

Attota, et al., Nanometrology using a through-focus scanning optical microscopy method, Measurement Science and Technology, 2011, pp. 1-10.

*Primary Examiner* — Michael P Stafira
(74) *Attorney, Agent, or Firm* — Cantor Colburn LLP (57) ABSTRACT

ProA wafer image inspection apparatus for inspecting defects of a semiconductor wafer comprises: a lighting portion for generating light; a lens portion for obtaining a wafer image, which is reflected after the light has been reflected onto a wafer to be inspected, and delivering the wafer image by lighting same in one direction; a dividing optical element for dividing the wafer image delivered from the lens portion; an image detection portion comprising a plurality of image-capturing elements, which are installed so that images which have passed through the lens portion and the dividing optical element are respectively formed on different focus positions; and an image processing portion for combining the images on different focus positions captured by the plurality of image pick-up elements to form a (Continued)

TSOM image, and comparing the TSOM image with a TSOM image of a normal semiconductor apparatus part to determine whether an object is defective.

13 Claims, 8 Drawing Sheets

(51) Int. Cl.
    *G01N 21/95*     (2006.01)
    *H01L 21/66*     (2006.01)

(52) U.S. Cl.
    CPC ............... *G01N 2021/8887* (2013.01); *G01N 2201/063* (2013.01); *H01L 22/12* (2013.01)

(58) Field of Classification Search
    CPC ............ G01N 21/94; G01N 21/95623; G01N 2021/8822; G01N 2021/8825; G01N 21/33; G01N 21/55; G01N 2021/95676; G01N 21/9503
    See application file for complete search history.

(56) References Cited

U.S. PATENT DOCUMENTS

| | | | |
|---|---|---|---|
| 7,355,689 B2 * | 4/2008 | Almogy | G01N 21/8903 250/208.1 |
| 7,417,721 B2 * | 8/2008 | Uto | G01N 21/9501 356/237.2 |
| 7,436,507 B2 * | 10/2008 | Moribe | G03F 1/84 356/237.4 |
| 7,573,569 B2 * | 8/2009 | Puah | H05K 13/08 356/237.2 |
| 7,714,997 B2 * | 5/2010 | Shibata | G01N 21/21 356/237.2 |
| 7,957,066 B2 * | 6/2011 | Armstrong | G02B 17/0812 356/237.2 |
| 8,203,706 B2 * | 6/2012 | Shibata | G01N 21/95623 356/237.2 |
| 8,804,111 B2 * | 8/2014 | Golovanevsky | G01N 21/9501 356/237.2 |
| 9,322,640 B2 * | 4/2016 | Koptyaev | G01B 11/02 |
| 9,360,662 B2 * | 6/2016 | Koptyaev | G02B 21/365 |
| 2012/0044486 A1 | 2/2012 | Chen et al. | |

FOREIGN PATENT DOCUMENTS

| | | |
|---|---|---|
| JP | 2000249900 | 9/2000 |
| JP | 2001227914 | 8/2001 |
| JP | 2009162593 | 7/2009 |
| JP | 2010019635 | 1/2010 |
| JP | 2012049381 | 3/2012 |
| KR | 100814628 | 3/2008 |
| KR | 20090026905 | 3/2009 |

\* cited by examiner

WAFER IMAGE INSPECTION APPARATUS

TECHNICAL FIELD

The present invention relates to a wafer inspection apparatus and, more particularly, to a wafer inspection apparatus capable of obtaining an image of a wafer part in which a semiconductor circuit has been formed, analyzing the image, and inspecting whether a defect is present in the wafer part.

BACKGROUND ART

In a wafer inspection apparatus for obtaining an image of a portion of a wafer and inspecting the image, in general, lighting having a single wavelength pulse is radiated to a corresponding area of the wafer while the wafer passes through a predetermined area for photographing (capturing image). Furthermore, a field of view (FOV) in which a lens unit may obtain an image is illuminated through a single piece of pulse lighting. Reflected light from the field of view passes through the lens unit, and an image of the photographing area (object area) of the wafer is focused on the pixel unit of an image pick-up element which functions as a screen at the back of the lens unit. After the photographing area of the wafer is photographed, in a next pulse lighting time, the wafer is moved so that a next photographing area adjacent to the photographed area is photographed.

In order to photograph all the areas of a wafer, assuming that a pulse lighting time is very short and the wafer is rarely moved during the pulse lighting time, the wafer has to move in the width direction during a pulse lighting cycle by the width of a field of view to be photographed, which may be once photographed by the image pick-up element.

However, to photograph a field of view to be photographed which has been radiated by lighting using a single image pick-up element requires a very long time taken to inspect the entire wafer because an existing image pick-up element has a limited capacity. Although a high-capacity image pick-up element is used, it is not appropriate because a lot of time is taken by a computer system connected to the image pick-up element and analyzing an image.

Accordingly, there is used an area sensor type wafer image inspection apparatus in which a plurality of unit image pick-up elements is disposed in the entire photographing unit so that they form a focal plane array (FPA) so as to increase a wafer area which may be photographed once and in which the image pick-up elements are analyzed using a single computer so as to reduce the time taken to inspect the wafer.

In the focal plane array, however, it is practically difficult to dispose a plurality of unit image pick-up elements closely. Row and column lead wires for drawing information signals, corresponding to images focused on pixel areas, to the outside need to be installed in each of the image pick-up elements in addition to the pixel areas to which the images are inputted. In order to install such lead wires, an installation area or an installation space around the pixel area is inevitable. If we take such a lead wire installation space into consideration, it is hard to think that the pixel areas of the plurality of image pick-up elements are closely disposed in a matrix form.

Accordingly, there is used a method for spatially separating and installing a plurality of unit image pick-up elements to be included in the virtual matrix of a unit image pick-up element which will be disposed in a focal plane on which an image of a photographing area of a wafer is focused, dividing the image to be focused on the focal plane for each area using an optical element, and distributing the split images to the respective image pick-up elements that are spatially separated and installed.

Figure 1:
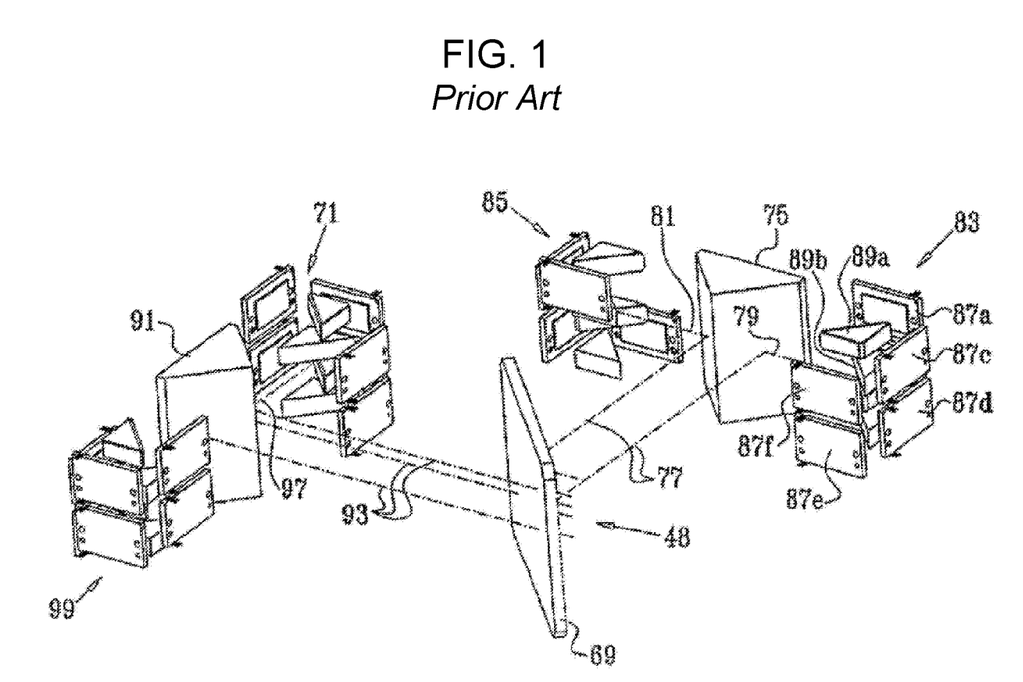
FIG. 1 is a diagram showing the configuration of some elements related to image division in a conventional wafer image inspection apparatus.

A wafer inspection apparatus for photographing the entire valid area of a wafer using spatially split image pick-up elements, analyzing a corresponding image, and detecting a defect using such a method is disclosed in Korean Patent No. 1113602 by Negevtech Ltd. A perspective view of FIG. 1 shows the concept of such a conventional wafer image inspection apparatus.

In such an apparatus, an image of a focal plane is split using a plurality of unit image pick-up elements forming the focal plane, that is, two-dimensional detectors 87a, 87c, 87d, 87e, and 87f and at least one optical element functioning to divide the image of the focal plane between the two-dimensional detectors using a beam splitter 69 of a glass plate form, prisms 89a, 89b, and 95, and a mirror.

In such an apparatus, in order to secure an accurate image of a field of view, the plurality of unit image pick-up elements is always disposed to form a focal plane array (FPA). An image other than the focal plane array is always the subject of resetting of equipment.

Meanwhile, in a semiconductor apparatus, a method for forming a circuit device by integrating circuit elements, such as devices and conducting wires, on a plane in a small size and continuing to reduce the size of the devices and wires so as to improve the degree of integration was used. However, as the degree of integration of devices is increased, it has become difficult to reduce the size of the devices and wires due to several limits in terms of a process for fabricating the semiconductor apparatus, for example, the optical limit of a photolithography process. Furthermore, to reduce the size of the devices has reached the state in which a device function may be problematic.

In such a condition, in order to improve the degree of integration of the devices of a semiconductor apparatus, a three-dimensional apparatus configuration, such as the multi-layering of the semiconductor apparatus and the three-dimension of the device configuration, is chiefly being attempted.

After a semiconductor apparatus is fabricated through a highly precise and complicated multi-stage process, an inspection task for checking whether the semiconductor apparatus has been normally formed as designed and whether the semiconductor apparatus may perform its unique function plays a very important role in discovering a process failure and finding out and correcting a problem so as to improve efficiency and effectiveness of the process.

Inspection equipment that belongs to pieces of existing semiconductor apparatus inspection equipment and that uses an image obtains an image of part of a target semiconductor apparatus and checks whether a semiconductor apparatus is defective by determining whether the image is normal. The three-dimensional configuration of semiconductor apparatuses has a problem in that an inspection cannot be performed sufficiently and properly using a conventional plane inspection method for the semiconductor apparatus.

If patterns are too small, it is difficult for a lighting beam to reach the patterns through the patterns. An optical microscope produces meaningful resolution results only if it is greater than half the size of a wavelength of light used. In the inspection of small patterns, such as the inspection of a semiconductor apparatus, a microscope user may uses a method for grouping and arranging similar patterns at a constant interval, observing how light is distributed between the groups, and determining the size. Such a method has many difficulties in measuring a new three-dimensional structure of semiconductor apparatuses.

A non-optical measuring method may be taken into consideration. It is difficult to use a non-optical image processing method, such as a scanning probe microscopy, as a practical inspection apparatus because the scanning probe microscopy is expensive and slow.

Recently, Ravikiran Attota, etc. who work for the National Institute of Standards and Technology (NIST) proposes a possibility that a three-dimensional fine pattern may be measured using a through focus scanning optical microscopy (TSOM). ("TSOM method for semiconductor metrology", Proc. SPIE 7971, Metrology, Inspection, and Process Control for Microlithography XXV, 79710T, Apr. 20, 2011).

In this technology, an existing optical microscope is used, but a method for collecting two-dimensional images of the same object at different focal positions and producing a three-dimensional image data space of the object is used. Accordingly, the obtained two-dimensional images form a through-focus image, including an in-focus image and some out-of-focus images. A computer performs processing on such a three-dimensional image data space. The computer extracts a brightness profile from a plurality of collected through-focus images of the same object and generates an image of a through-focus scan optical microscope (TSOM) using information about the focal positions.

An image provided by the TSOM does not represent the object as it appears unlike a common photo (captured image). Although the images are abstract a little, a difference between the fine shapes of a measured target three-dimensional structure may be deduced based on a difference between the images.

Simulation research revealed that the TSOM is capable of measuring characteristics of 10 nanometers or less. The TSOM proposes the possibility of analyzing the shape of a fine three-dimensional structure.

However, to obtain optical images having many different focal positions with respect to a very small object is a task requiring a lot of time. A method which solves problems and which is substantially used for the illumination of a semiconductor apparatus has not yet been properly proposed.

DISCLOSURE

Technical Problem

An object of the present invention is to provide a wafer inspection apparatus in which a stage where a wafer is placed or a lens unit for obtaining an image of a wafer is not moved and a plurality of images at different focal positions can be obtained substantially at the same time.

Such a plurality of images having different focal positions enables a through-focus scan optical microscope (TSOM) image to be obtained so that a three-dimensional inspection can be performed on the fine patterns of a wafer.

Accordingly, an object of the present invention is to provide a wafer inspection apparatus capable of determining whether a three-dimensional fine pattern of a wafer is defective using an existing optical wafer inspection apparatus.

An object of the present invention is to provide a wafer inspection apparatus capable of rapidly determining whether a three-dimensional fine pattern is defective at a low cost using an existing optical wafer image inspection apparatus.

Technical Solution

The present invention for achieving the above objects provides a wafer image inspection apparatus for obtaining and inspecting an image of a semiconductor wafer so as to inspect a defect in the semiconductor wafer, wherein an image beam for a part to be inspected is split and a plurality of images having different focal positions is obtained at the same time.

More specifically, the apparatus of the present invention includes a lighting unit which generates lighting, a lens unit which obtains an image of a target inspection wafer reflected after the lighting is radiated to the wafer and projects and transfers the image in one direction, an image detection unit which includes a split optical element for splitting the image of the wafer transferred by the lens unit and a plurality of image pick-up elements installed so that an image passing through the lens unit and the split optical element is formed on different focal positions, and a through focus scanning optical microscopy (TSOM) image processing unit which forms a TSOM image by combining the images of the different focal positions captured by the plurality of image pick-up elements and determines whether the target inspection wafer has a defect by comparing the TSOM image with a TSOM image of a normal pattern for the target inspection wafer.

In the present invention, a focusing optical system may be disposed between the split optical element and the image pick-up elements so that the images of the different focal positions are focused on the image pick-up elements of the image detection unit in accordance with a plurality of respective images split by the split optical element. The focusing optical system is part of the whole lens unit and may be installed so that the focusing optical system forms a second lens unit, for example.

As described above, in the present invention, the position between lenses may be controllable. The different focal positions may be implemented using lenses or a lens assembly having different focal lengths in the focusing optical system or by differently installing the distance between the same focusing optical system and each of the image pick-up elements. The lens assembly having the different focal lengths may be configured by controlling the distance between the lenses of the same lens assembly or replacing at least some of lenses with other lenses having different focal distances.

In the present invention, the lighting unit may include a pulse laser.

In the present invention, the split optical element may include one or more beam splitters or mirrors.

In the present invention, the TSOM image processing unit may include a TSOM image formation unit and a TSOM image comparison and determination unit. The TSOM image formation unit may be configured to extract a brightness profile of two-dimensional images having the different focal positions obtained by the plurality of image pick-up elements and to generate the TSOM image using information about the focal positions. The image comparison and determination unit may be configured to determine whether an object is defective by comparing the TSOM image obtained by the TSOM image processing unit with a TSOM image of a normal semiconductor apparatus part. The TSOM image processing unit may be configured to include an image processing program and a processor for processing image information and may be commonly implemented using a equipment-dedicated computer.

In the present invention, the wafer image inspection apparatus may be equipped with a wafer movement stage for holding and moving the wafer and a signal generation unit for controlling moving speed of the wafer movement stage so that an image detection position, that is, a position where the wafer is exposed to the lighting, is associated with the pulse generation cycle of the lighting.

In the present invention, the image pick-up element or image sensor may include a CCD or CMOS type unit image pick-up element.

Advantageous Effects

In accordance with the present invention, when the split optical element which receives an image of a wafer generated by the radiation of lighting from the lens unit generates a plurality of images, the focusing optical system between the split optical element and the image pick-up elements can generate a plurality of images having different focal positions by using different focal distances or controlling the distance between the focusing optical system and the image pick-up elements.

In accordance with the present invention, a semiconductor apparatus inspection for detecting a defect in a three-dimensional fine pattern by processing a plurality of images having different focal positions using a processing apparatus is made possible.

MODE FOR INVENTION

Hereinafter, the present invention is described in more detail in connection with embodiment with reference to the accompanying drawings.

Figure 2:
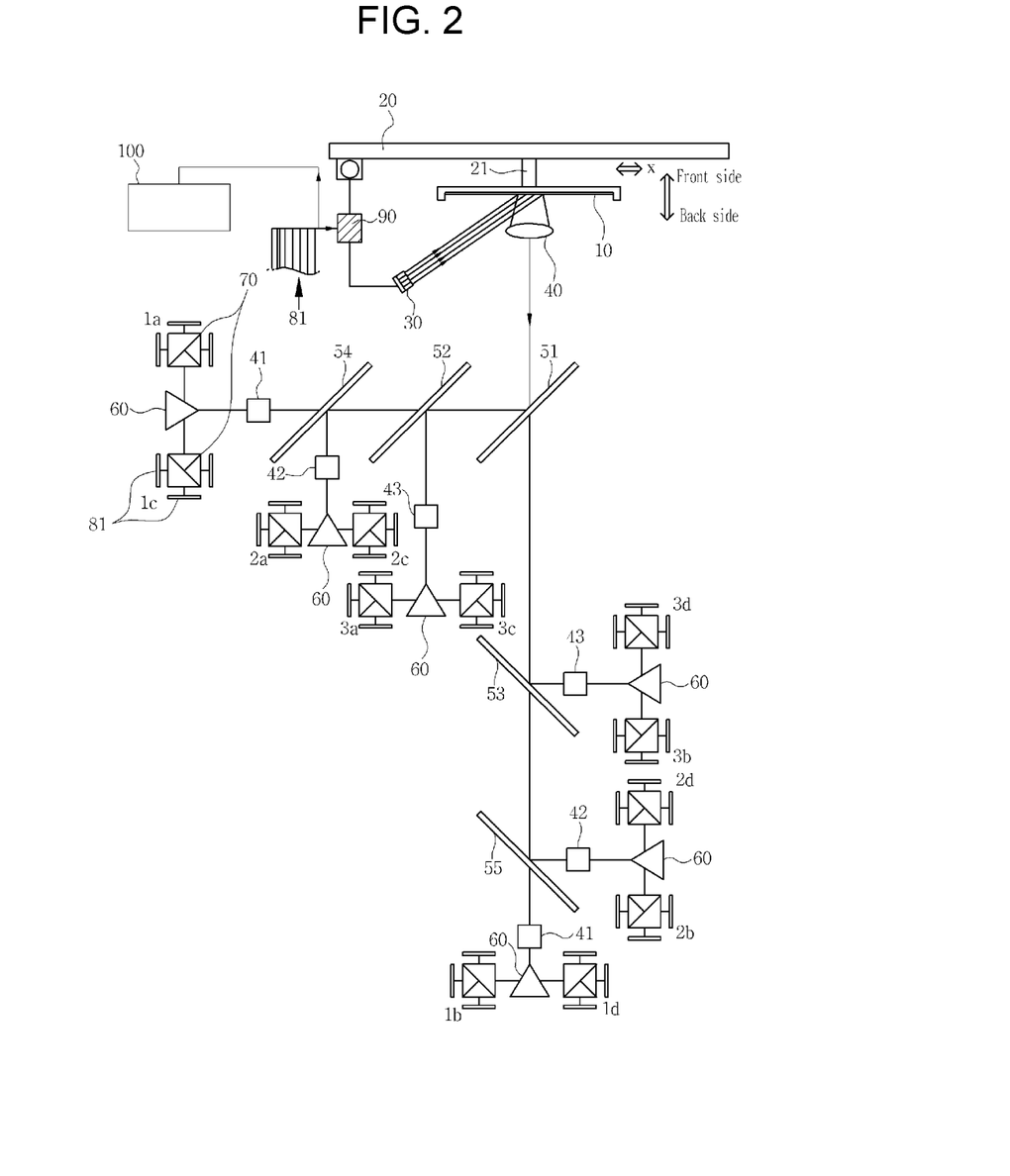
FIG. 2 is a conceptual diagram showing the general configuration of a wafer image inspection apparatus in accordance with an embodiment of the present invention.

FIG. 2 is a conceptual diagram simplifying and schematically showing the configuration of major elements of the present invention.

A configuration of a wafer image inspection apparatus according to the present invention is described through the present embodiment. A wafer 10 has been held by the wafer fixing chuck 21 of a wafer stage 20 or wafer movement stage and may move in the x-axis and y-axis directions on a plane parallel to the plane of the wafer. In this case, the wafer 10 consecutively moves in the x direction of an arrow. Such a wafer stage has been used as substantially the same method in several pieces of equipment for wafer processing, and a detailed configuration thereof is omitted.

Figure 3:
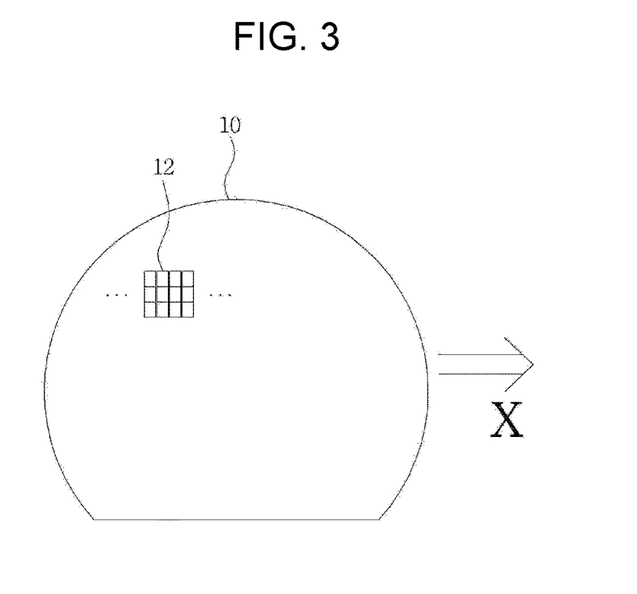
FIG. 3 is a plan view showing a wafer of which the photographing area inspected in accordance with an embodiment of the present invention.

FIG. 3 shows a field of view to be photographed, which is photographed once on the wafer 10 and includes a 3×4 matrix of unit areas 12.

The areas include four columns a, b, c, and d, and three unit fields of view are arranged in each column up and down.

If an image detection position to which a light source radiates light at a specific interval is fixed and the wafer moves in the wafer stage in the x-axis direction as shown by the arrow, when light of a next cycle is radiated to the wafer, four columns placed right on the left of shown four columns are placed in the image detection position.

If the distance obtained by multiplying moving speed of the wafer by the light-emitting cycle of the light source is equal to the width of a photographing area that is once photographed (the width of the four columns), a captured image may represent the entire wafer without an overlapped area or an omitted area on the wafer.

Figure 4:
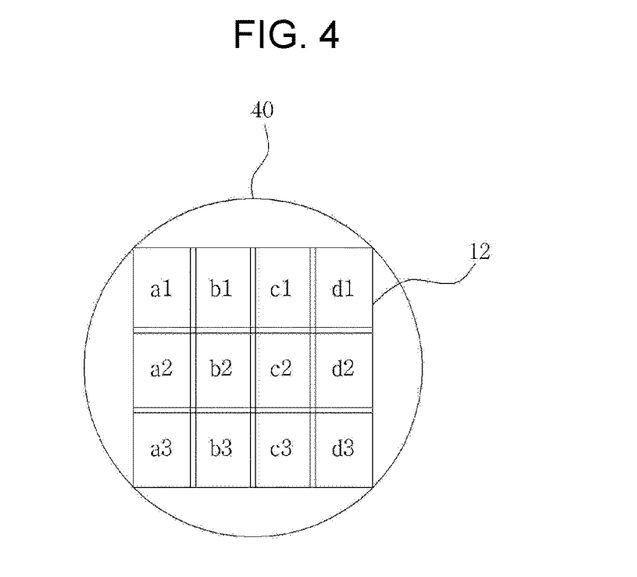
FIG. 4 is a diagram showing an image of the wafer the photographing area which is projected through a lens unit in accordance with another embodiment of the present invention.

FIG. 4 shows an image of the field of view of the wafer which may be checked through a lens unit.

An image 12' of a unit field of view is shown and forms a 3×4 matrix. The image of the wafer forming the 3×4 matrix is backward projected through a first lens 40.

Lighting L is radiated so that a field of view to be photographed is included in the current position of the wafer 10. If an image is to be obtained while the wafer stage is driven at high speed so as to inspect the wafer at high speed, a flash, a strobe light type, or a laser beam light may be used because an image capturing time becomes very short and thus lighting having strong light (having high energy) needs to be generated within a short time.

In this case, a laser 30 is used as the light source of the lighting. In order to use laser beam lighting, a pulse laser generating strong energy within several microseconds needs to be used. A laser beam energy generation time and an image capturing time need to be synchronized as described above. The laser radiates a laser pulse to a light radiation area in response to a trigger signal.

In a prior art, a flash lamp is chiefly used, the laser rarely generates the number of pulses of 120 Hz per second, and high maintenance and management costs are required. Recently, as a solid state laser pumped by a diode laser is used, a durability life is increased, maintenance and management costs are reduced, and a pulse generation cycle of 1000 Hz or more is made possible. Accordingly, inspection speed of the entire wafer can be increased because moving speed of the wafer can be increased that much. Even in this case, such a diode laser pumping solid laser is used.

In the wafer part to which lighting is radiated, reflection light reflected by a surface of the wafer 10 travels in all surrounding directions. In view of the path of light, the lens unit is installed at the back of the corresponding area of the wafer 10, and an image of the field of view of the wafer included in the reflection light is projected to the back of the lens unit through the lens unit.

The lens unit may include a single lens, but may include a lens assembly of a plurality of lenses. The lens unit is not installed at a single place, but may be distributed on the optical path. In this case, the lens unit is split into a first lens unit 40 at the back of the wafer and a second lens unit at the back of beam splitters 52, 53, 54, and 55 forming a split optical element or focusing optical systems 41, 42, and 43.

In general, the first lens unit 40 functions as a convex lens for enlarging the field of view of the wafer. If the distance between the center of the convex lens and the field of view is controlled, an image projected on the back of the first lens unit 40 may have a constant size regardless of the distance between the first lens unit 40 and an image detection unit.

The projected image of the field of view to be photographed is split into reflection light and transmission light by the first beam splitter 51. In this case, the section of the image is not split in the width or height (up and down) direction, but is split into images of the entire two areas in the state in which the amount of light has been reduced by reflectance and transmittance of the beam splitter 51. The split reflection light and transmission light are respectively projected on the second beam splitter 52 and the third beam splitter 53.

The reflection light incident on the second beam splitter is split into transmission light and reflection light again. The transmission light is incident on the fourth beam splitter 54 and split into transmission light and reflection light again. The three pieces of light split as described above pass through the focusing optical system (the second lens units 41, 42, and 43) having different focal distances. They are split into two columns (the column a and the column c) through a prism (or mirror) 60 for dividing an image laterally (in the width direction) and are then incident on up and down division mirror units 70.

The transmission light incident on the third beam splitter 53 is split into transmission light and reflection light again. The transmission light is incident on the fifth beam splitter 55 and split into transmission light and reflection light again. The three pieces of light split as described above also pass through the focusing optical system 41, 42, and 43 having different focal distances. They are split into two columns (the column b and the column d) through the prism (or mirror) 60 and are then incident on the up and down division mirror units 70.

In this case, the reason why two columns placed with one column interposed therebetween not between neighboring columns are split into the up and down division mirror units and the prism 60, that is, a single optical element for width division, projects images is for projecting complete images of the respective columns on the up and down division mirror units 70 so as to prevent the distortion of an image in a division edge (corner) part of the prism if two neighboring columns are split using the edge part of the prism.

Figure 5:
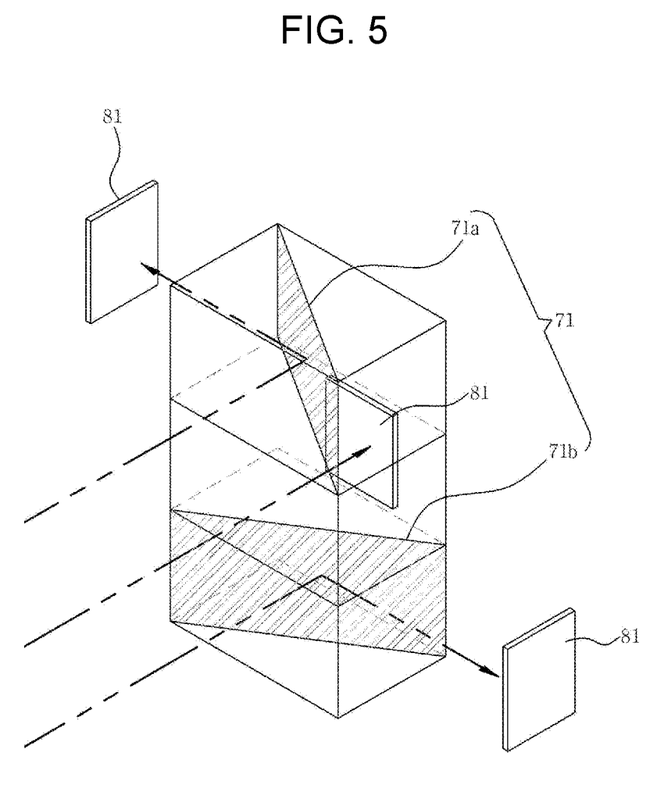
FIG. 5 is a perspective view schematically showing the configuration of an up and down division mirror unit and an image detection unit in accordance with an embodiment of the present invention.

As shown in FIG. 5, images of three unit fields of view to be inspected (assuming that a1, a2, and a3 in the column a of a field of view to be inspected, such as FIG. 4) split for each up and down section by the up and down division mirror units are projected on the unit image pick-up element 81 of the image detection unit.

Accordingly, in the present embodiment, an image is split into 12 stems. Each of the stems includes three unit fields of view to be inspected, which correspond to a single column for each stem and which are arranged up and down. As a result, a total of 36 image pick-up elements are installed.

In the above embodiment, each of the columns (the column a, the column b, the column c, and the column d) obtains three images (in the case of the column a, 1a, 2a, and 3a) at different focal positions through three types of focusing optical systems 41, 42, and 43 having different focal distances. Accordingly, a unit field of view to be inspected, which belongs to each column, has three images at different focal positions. If the three images of different focal positions are processed by the TSOM image processing unit 100 of a computer in the image pick-up element, a TSOM image of each unit field of view to be inspected (in this case, a total of 12 unit fields of view to be inspected) is obtained.

The images projected from the prism 60 for width division to the respective up and down division mirror units 70 correspond to images of three wafer unit areas in the up and down direction which have been arranged in the column direction.

The up and down division mirror units 70 include an up and down division mirror 71 (71a and 71b) inclined 45 degrees in the left and right direction with respect to an incident image corresponding to a single column including an array of three fields of view to be captured on the wafer. Accordingly, the images of the wafer unit areas are projected on respective image pick-up elements 81 on the left and right in the travel direction of the images. One of the images of the three unit areas forming a column travels without reflection and is projected on a corresponding image pick-up element 81.

FIG. 5 shows the state in which an image of each column is split up and down by the up and down division mirror units 70 and the split three images are projected on the unit image pick-up element 81 or the unit image detection unit. A mirror 71a, 71b for reflecting an image so that an image of a unit area placed at the top in each column turns left or an image of a unit area placed at the bottom in each column turns right may be constructed by forming a reflection layer in an inclined plane of a triangle prism.

In this case, the image detection unit includes complementary metal oxide semiconductor (CMOS) type image pick-up elements 81 which are respectively distributed on the left, right, and back of the up and down division mirror unit and each of which has a unit 4 megapixels capacity. A conventional CCD type image pick-up element has low image acquisition speed to obtain an image of a large-area wafer because "an image that may be grabbed per second (hereinafter called a frame per second (fps))" is about 60 frames or less. In contrast, a recent camera on which a CMOS sensor of 4M pixels has been mounted can obtain 240 image frames or more per second even using a CMOS sensor because the technology of the image pick-up element is advanced.

In general, the unit image pick-up element may include an image pick-up element, such as a CCD. The image pick-up element receives an image projected on a pixel unit having a plurality of pixels of a matrix form and generates a digital image signal using the received image. The digital image signal is inputted to an image processing apparatus or image processing means (not shown) capable of detecting an error of a semiconductor apparatus through a display, such as a computer.

In this case, the TSOM image processing unit extracts a brightness profile from every three images having different focal positions with respect to each of obtained unit fields of view and generates a through-focus scan optical microscope (TSOM) image using information about the focal positions of the three images.

So as to obtain images of the object having different focal positions, information about focal positions may be used. The positions of the object, the lens, and the image pick-up element in the apparatus of the present invention may be controlled by using a relationship of Equation 1 among enlargement magnification Mag of the lens, a projection direction distance $dZ_{FPA}$ based on FPA of the image pick-up element and a direction distance change $dZ_{wafer}$ in the depth of focus of a three-dimensional fine pattern, that is, the object to be inspected. This may be performed by incorporating a program for controlling a mechanical device which moves the object, the lens, or the image pick-up element in the projection direction or focal direction of an image.

$$dZ_{FPA} = Mag^2 * dZ_{wafer} \quad \text{[Equation 1]}$$

If a wavelength λ of light used in the apparatus of the present invention is 760 nm (nanometers) corresponding to visible ray red or near-infrared rays and an aperture ratio NA related to lens magnification is 0.6, assuming that a difference in the depth of focus (DOF) of the object is 1 micrometer and enlargement magnification is 36 according to Equation 2 below, $dZ_{FPA}$ is 1.3 mm according to Equation 1 above.

$$DOF(1 \, \mu m) = \lambda/2NA^2 \quad \text{[Equation 2]}$$

Furthermore, the image comparison and determination unit of the computer checks and determines whether a defect is present in the pattern of a corresponding unit field of view to be inspected by comparing the TSOM image with a TSOM image of the normal pattern of a corresponding area already stored in computer memory.

In this case, although a method of generating the TSOM image and checking a difference between the fine patterns through a comparison is not described in detail, to detect a fine difference of a level of several tens of nanometers between two three-dimensional objects by performing a comparison on the TSOM images obtained by processing a plurality of optical microscope images at different focal positions with respect to the same three-dimensional object has already been known in the art, and thus a detailed description thereof is omitted.

In the aforementioned embodiment, the focusing optical systems 41, 42, and 43 have been illustrated as being lenses (lens assembly) having different focal lengths. In an embodiment, lenses having the same focal length are used, but the distance between the lens and the image pick-up element 81 (the distance on the optical path) may be different based on the FPA or the distance between the lenses forming the focusing optical system may be controlled so as to obtain images of unit fields of view to be inspected, which have different focal positions.

In this case, although not shown, a lead wire and a circuit unit for transferring an image digital signal to the outside are formed in the surroundings of the rectangular pixel unit of a unit CMOS type image pick-up element. An image signal obtained by the image pick-up element is inputted to image processing means (not shown), such as a computer, so as to determine whether a defect is present in a semiconductor apparatus inspected through image processing.

In general, the image processing means includes a computer system including a processor and an image processing program included in the computer system. The image processing program is a kind of image processing program and configured to detect an abnormal portion by comparing a pattern with a previously inputted normal pattern.

The image processing means may be configured to include a plurality of terminals (not shown) for receiving images detected by the unit image pick-up elements 81 of the image detection unit and processing the images and a master terminal (not shown) for collecting the images processed by the terminals and finally detecting whether a defect is present in the wafer. If image processing speed of each terminal is low, an image division unit for distributing an image detected by the unit image pick-up element of the image detection unit into a plurality of paths and sending the images to respective terminals for image processing for a faster inspection may be further included.

Meanwhile, there is installed a trigger signal generation unit 90 for controlling moving speed of the wafer 10 of the wafer stage 20 by associating the pulse cycle of the laser 30 generating lighting with moving speed of the wafer 10 in the wafer stage 20 in such a manner that the wafer 10 is moved in the X-axis direction by the width of an existing photographing area when a next laser pulse is radiated while the wafer 10 is moved at constant speed so that a next photographing area is accurately photographed by the image pick-up element.

A signal associated with the image digital signal of the image detection unit may be inputted through the computer or from the unit image pick-up element directly to the trigger signal generation unit 90 that drives the wafer stage so as to control moving speed of the wafer and for synchronization between a laser pulse and photographing.

That is, the trigger signal generation unit 90 generates the driving signal of the wafer stage 20 that moves the wafer and the control signal of the laser 30 providing lighting and controls a photographing area projected on the image detection unit using the signals so that the photographing area is not overlapped or omitted.

The image pick-up element may be configured so that an image of the wafer is automatically captured without a separate signal when lighting is radiated to the wafer area and the image is inputted to the pixel unit, but may capture an image only when a signal is received in response to a signal synchronized with lighting. For example, the trigger signal generation unit 90 provides a caption control signal to the image detection unit and the laser 30 that provides lighting so as to obtain an image of the wafer.

Accordingly, position data to which an inspection position has been mapped is stored in the control apparatus of a lower stage. When the stored mapping data reaches the corresponding position, a trigger signal for image capturing and the turn-on of the lighting of the lighting unit is generated. The generated trigger signal is configured to generate an accurate synchronization signal for lighting and image capturing in the trigger signal generation unit, and thus an image capturing signal and a lighting generation signal can be separately output.

Figure 6:
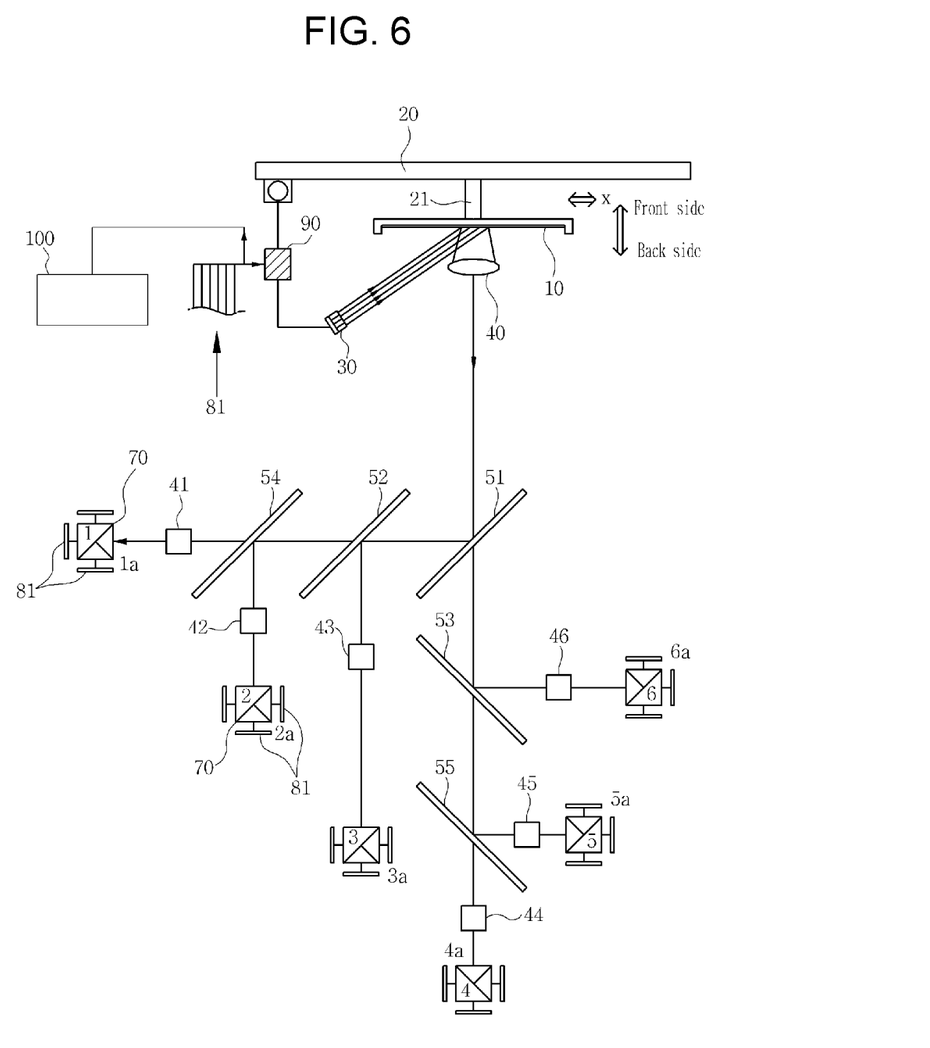
FIG. 6 is a conceptual diagram showing the general configuration of a wafer image inspection apparatus in accordance with another embodiment of the present invention.

FIG. 6 is a diagram showing another embodiment of the present invention.

In this case, another embodiment of the present invention is different from the previous embodiment in a split optical element and an image detection unit.

That is, in the previous embodiment, a field of view to be photographed which is projected includes 12 unit fields of view to be inspected in a 3*4 matrix. An image of the field of view is split into reflection light and transmission light repeatedly and sequentially by the first to fifth beam splitters. The six pieces of the light split as described above pass through three types of focusing optical systems (the second lens units) having different focal distances and are split into two columns through the prism (or mirror) for splitting an image laterally (in the width direction), thereby forming a total of 12 beams. Each of the 12 beams is incident on the up and down division mirror units 70, split into three directions of the left, right, and front, and inputted to 36 image pick-up elements. An image of each of the unit fields of view to be inspected becomes three images of different focal positions through the three types of the focusing optical systems.

However, in the embodiment of FIG. 6, a field of view to be photographed which is projected includes three unit fields of view to be inspected, which form a single column (column b). As in the previous embodiment, an image of the field of view is split into reflection light and transmission light repeatedly and sequentially by first to fifth beam splitters 51, 52, 53, 54, and 55. The six pieces of the light split as described above pass through six types of focusing optical systems (second lens units 41, 42, 43, 44, 45, and 46) at different focal distances, respectively, but do not pass through a prism (or mirror) for splitting an image laterally (in the width direction). Accordingly, the six pieces of the light form six beams. Each of the six beams is incident on the up and down division mirror units 70, split in three directions of the left, right, and front, and inputted to 18 image pick-up elements 81. As a result, an image of each of three unit fields of view to be inspected included in a column passes through six types of focusing optical systems, thus becoming six images at different focal positions.

When six images of different focal positions of three unit fields of view to be inspected, which have been obtained by the image pick-up element, are obtained whenever a laser pulse is radiated to the wafer, the images are sent to the computer of the apparatus and processed by the TSOM image processing unit. Accordingly, a TSOM image of a unit field of view to be inspected (in this case, a total of three unit fields of view to be inspected) is obtained.

In this case, the capacity of each image pick-up element can be increased a little and thus images can be processed at once because the number of image pick-up elements is small compared to the previous embodiment. The image pick-up element includes complementary metal oxide semiconductor (CMOS) type image pick-up elements each having a capacity of 12 megapixels of 4000×3000 in length and breadth.

Figure 7:
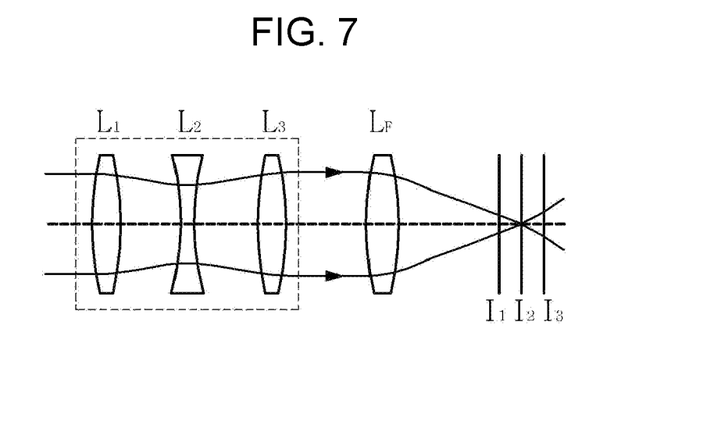
FIG. 7 is a conceptual diagram showing a focusing optical system in accordance with yet another embodiment of the present invention.

FIG. 7 is a conceptual diagram showing a focusing optical system in accordance with yet another embodiment of the present invention.

In this case, a lens assembly, including afocal zoom systems $L_1$, $L_2$, and $L_3$ commonly called zoom lens systems and a focal lens $L_F$, is installed as the focusing optical system.

The entire position where the lens assembly is installed and the positions of image pick-up elements $I_1$, $I_2$, and $I_3$ are displayed. In this case, in order to obtain images of different focal positions for the same object, the distance between the focal lens $L_F$ and the image pick-up elements $I_1$, $I_2$, and $I_3$ has been illustrated as being different.

Although not shown, images at different focal positions may be obtained if different focal lenses are adopted in a plurality of lens assemblies in order to make their focal distances different and image pick-up elements are disposed so that the distances between the focal lens and each of the image pick-up elements are the same.

Figure 8:
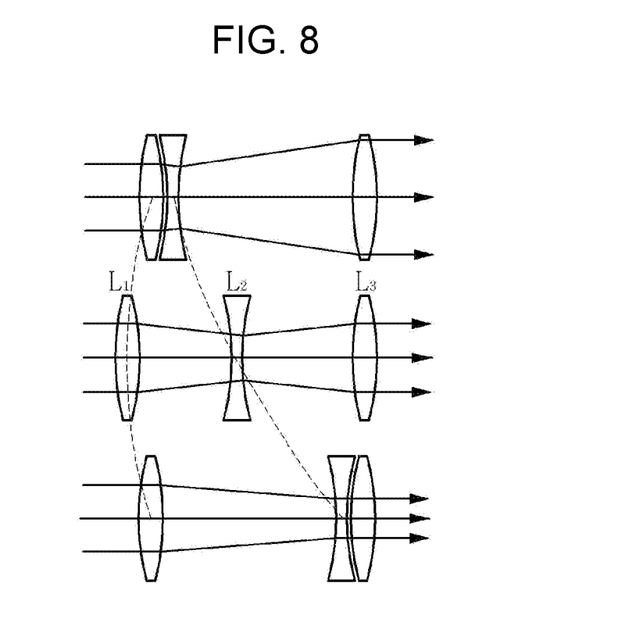
FIG. 8 is a conceptual diagram showing a position between lenses forming the afocal zoom system of the focusing optical system and a change in the sizes of the phases of the lenses in the embodiment of FIG. 7.

In such a configuration, images of different focal positions having a difference of magnification are obtained by changing the positions of the lenses $L_1$ and $L_2$ of the afocal zoom systems $L_1$, $L_2$, and $L_3$ as in FIG. 8, and a TSOM image of a field of view is obtained by inspecting the images. In a semiconductor apparatus, an actual field of view may be widened or narrowed depending on a difference of magnification.

If magnification is increased, a method of reducing moving speed of the wafer in the wafer stage by associating magnification with the moving speed or of increasing the number of radiations of a laser pulse per second may be used in order to inspect the entire semiconductor apparatus without omission.

In accordance with such a configuration, an inspection can be performed by controlling only the positions of some of the lenses $L_1$ and $L_2$ forming the afocal zoom system using an automatic control method, such as control of the zoom lens of an existing afocal zoom system, while changing magnification, that is, the size of a field of view to be inspected, if necessary without controlling the position where the image pick-up element is mounted or the general position of the focusing optical system.

Figure 9:
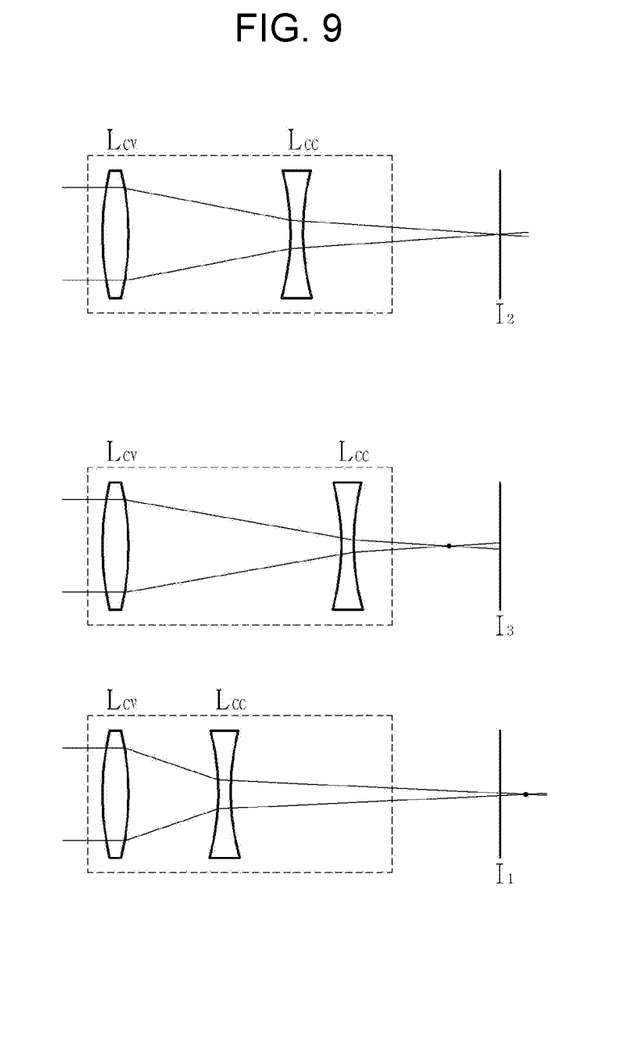
FIG. 9 is a conceptual diagram showing a focusing optical system in accordance with yet another embodiment of the present invention.

FIG. 9 is a conceptual diagram showing a focusing optical system in accordance with yet another embodiment of the present invention.

In this case, in a lens assembly including one convex lens $L_{CV}$ and one concave lens $L_{CC}$, the position of the convex lens $L_{CV}$ is fixed, and the position of the concave lens $L_{CC}$ is movable. When the concave lens $L_{CC}$ moves, the focal distance of the entire lens assembly of the focusing optical system is changed. Accordingly, although the positions of image pick-up elements $I_1$, $I_2$, and $I_3$ are fixed, images of fields of view to be inspected at different focal positions can be obtained by controlling the distance between the lenses of the lens assembly, and a TSOM image can be obtained by combining the obtained images.

In the state in which the lens assembly is installed in one main tube and the position of the main tube is not changed, if the position of the concave lens $L_{CC}$ or convex lens $L_{CV}$ or both of the main tube changes, a plurality of images having different focal positions can be obtained without changes of relative positions between the main tube and the image pick-up elements $I_1$, $I_2$, and $I_3$ forming the lens assembly in the wafer image inspection apparatus, and the degree of a distance between positions in the focuses of the images can also be controlled.

Figure 10:
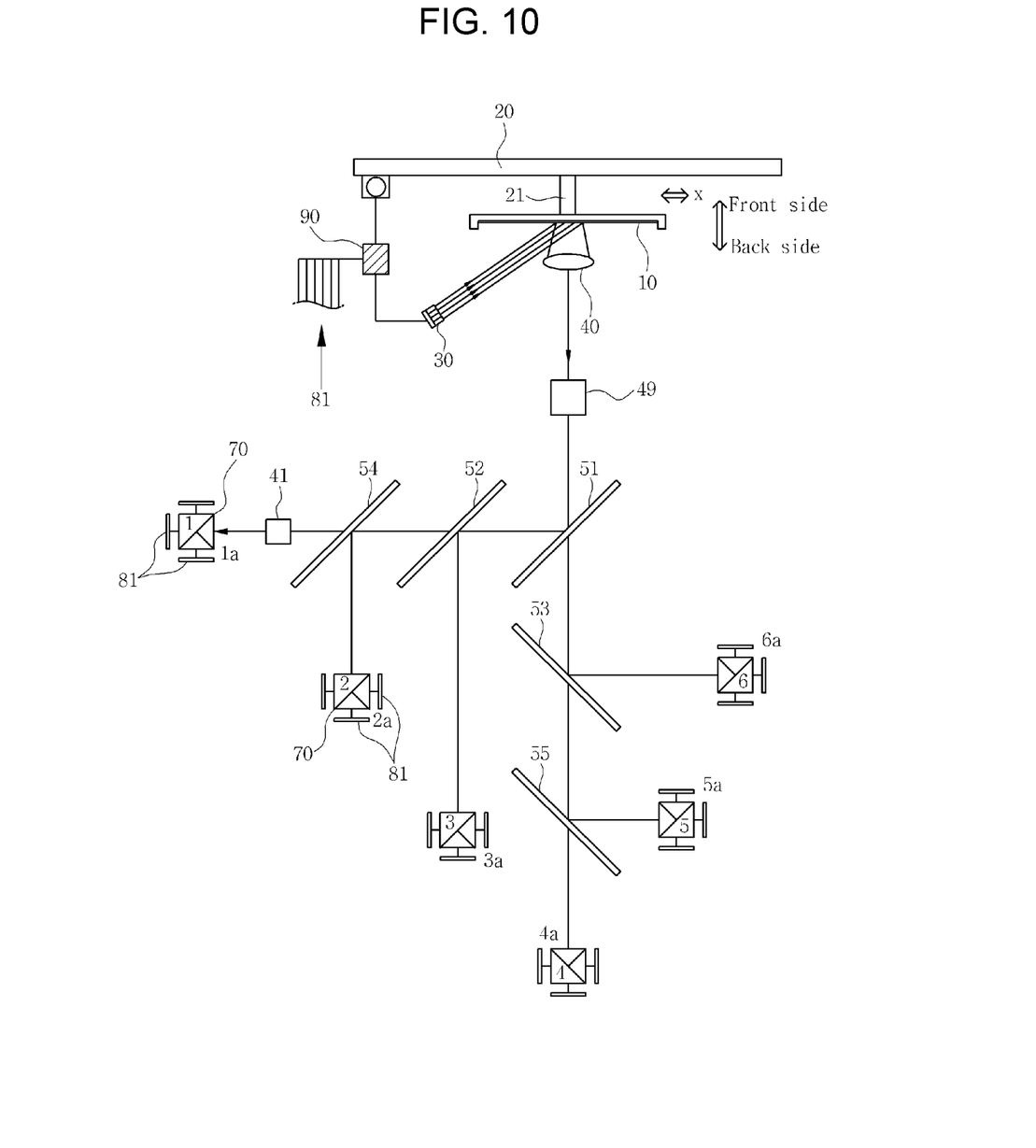
FIG. 10 is a conceptual diagram showing the general configuration of a wafer image inspection apparatus in accordance with yet another embodiment of the present invention.

FIG. 10 is a conceptual diagram showing the general configuration of a wafer image inspection apparatus in accordance with yet another embodiment of the present invention.

In this case, the wafer image inspection apparatus has a configuration generally similar to that of FIG. 6. A focusing optical system, for example, a lens assembly 49 including afocal zoom systems $L_1$, $L_2$, and $L_3$ commonly called zoom lens systems and a focal lens $L_F$, such as those shown in FIG. 7, is not installed after the split optical element, but is installed ahead of the split optical element so that the lens unit is placed between the wafer and the split optical element.

Accordingly, a plurality of focusing optical systems installed in accordance with all beams divided by the split optical element has been replaced with a single common focusing optical system. Furthermore, in such an embodiment, the positions of image pick-up elements are controlled and the distance between the lens unit and each of the plurality of image pick-up elements on the optical path is different so that the image pick-up elements may obtain respective images of different focal positions.

In such an embodiment, if the position of each of the image pick-up elements is determined, an inspection can be conveniently performed by controlling only the positions of some of the lenses $L_1$ and $L_2$ forming the afocal zoom system of a common focusing optical system using an automatic control method, such as control of the zoom lens of an existing afocal zoom system, depending on magnification, that is, the size of a field of view to be inspected, if necessary, without controlling the position in which the image pick-up element is mounted or the general position of the focusing optical system.

As described above, although the preferred embodiments of the present invention have been described and shown, the present invention is not limited to the shown and described configurations. Rather, those skilled in the art will well understand that the present invention may be changed and modified in various ways within the scope of the appended claims. Accordingly, all such proper modifications and equivalents should be construed as belonging to the scope of the present invention.

The invention claimed is:

1. A wafer image inspection apparatus for obtaining and inspecting an image of a semiconductor wafer so as to inspect a defect in the wafer, the wafer image inspection apparatus comprising:
   a lighting unit which generates lighting,
   a lens unit which obtains an image of a target inspection wafer reflected after the lighting is radiated to the wafer and projects and transfers the image in one direction,
   an image detection unit which comprises a split optical element for splitting the image of the wafer transferred by the lens unit and a plurality of image pick-up elements installed so that an image passing through the lens unit and the split optical element is formed on different focal positions, and
   a through focus scanning optical microscopy (TSOM) image processing unit which forms a TSOM image by combining the images of the different focal positions captured by the plurality of image pick-up elements and determines whether the target inspection wafer has a defect by comparing the TSOM image with a TSOM image of a normal pattern for the target inspection wafer.

2. The wafer image inspection apparatus of claim 1, wherein a focusing optical system is disposed between the split optical element and the image pick-up elements so that the images of the different focal positions are focused on the image pick-up elements of the image detection unit in accordance with a plurality of respective images split by the split optical element.

3. The wafer image inspection apparatus of claim 2, wherein in order to obtain the images having the different focal positions, the focusing optical system uses lenses having different focal distances in accordance with the plurality of respective images split by the split optical element or uses a different distance between the focusing optical system lens and the image pick-up elements.

4. The wafer image inspection apparatus of claim 1, wherein:
   the lighting unit comprises a pulse laser, and
   the split optical element comprises one or more beam splitters or mirrors and comprises a wafer movement stage for holding and moving the wafer and a signal generation unit for controlling moving speed of the wafer movement stage so that an image detection position which is a position where the wafer is exposed to the lighting is associated with a pulse generation cycle of the lighting.

5. The wafer image inspection apparatus of claim 1, wherein a distance between lenses forming the lens unit is controllable.

6. The wafer image inspection apparatus of claim 5, wherein:
   the lenses forming the lens unit are limitedly placed between the wafer and the split optical element, and
   the plurality of image pick-up elements has different distances from the lens unit on an optical path and is placed at different focal positions in order to obtain the images of the different focal positions.

7. The wafer image inspection apparatus of claim 6, wherein:
   the lens unit comprises lenses forming an afocal zoom system and a focal lens, and
   a distance between the lenses forming the afocal zoom system is controllable so that a size or enlargement magnification of a field of view to be inspected is controllable.

8. The wafer image inspection apparatus of claim 5, wherein:
   the lens unit comprises a first lens unit which obtains the image of the target inspection wafer reflected after the lighting is radiated to the wafer and projects and transfer the image in one direction and a plurality of second lens units respectively installed in accordance with a plurality of images split by the split optical element,
   a distance between the lenses forming the second lens unit is controllable, and
   the image detection unit is installed so that images passing through the first lens unit, the split optical element, and the second lens unit are focused on different focal positions.

9. The wafer image inspection apparatus of claim 8, wherein in order to obtain the images of the different focal positions, the lenses forming the plurality of second lens units have an identical type, but have different distances between the lenses so that the focal distances are different.

10. The wafer image inspection apparatus of claim 8, wherein in order to obtain the images of the different focal positions, the lenses forming the plurality of second lens units have an identical type and have an identical distance between the lenses, but distances between the plurality of second lens units and the plurality of image pick-up elements are different.

11. The wafer image inspection apparatus of claim 8, wherein in order to obtain the images of the different focal positions, the lenses forming the plurality of second lens units have an identical distance between the lenses, but have different types so that the focal distances are different.

12. The wafer image inspection apparatus of claim 10, wherein:
   the second lens unit comprises lenses forming an afocal zoom system and a focal lens, and
   a distance between the lenses forming the afocal zoom system is controllable so that a size or enlargement magnification of a field of view to be inspected is controllable.

13. The wafer image inspection apparatus of claim 5, wherein:
   the lighting unit comprises a pulse laser, and
   the split optical element comprises one or more beam splitters or mirrors and comprises a wafer movement stage for holding and moving the wafer and a signal generation unit for controlling moving speed of the wafer movement stage so that an image detection position which is a position where the wafer is exposed to the lighting is associated with a pulse generation cycle of the lighting.

* * * * *